United States Patent [19]

Goodrich et al.

[11] 4,084,434
[45] Apr. 18, 1978

[54] APPARATUS FOR DETERMINING DENIER OF YARN

[75] Inventors: Lewis Charles Goodrich, Wilmington; Theron Robert Holt, Newark; Joseph Cyril Osborne, Wilmington, all of Del.; Donald Kirk Pusey, West Grove, Pa.; James William Roxlo, Rockaway, N.J.

[73] Assignee: E. I. Du Pont de Nemours and Company, Wilmington, Del.

[21] Appl. No.: 782,325

[22] Filed: Mar. 29, 1977

[51] Int. Cl.$^2$ .......................................... D01H 13/32
[52] U.S. Cl. ......................................... 73/160; 57/56
[58] Field of Search ................... 73/160; 57/56, 34.5; 83/100

[56] References Cited

U.S. PATENT DOCUMENTS 3,820,430   6/1974   Hautemont ........................ 83/100

FOREIGN PATENT DOCUMENTS 6,931,296   8/1969   Germany.

Primary Examiner—Richard C. Queisser
Assistant Examiner—Joseph W. Roskos

[57] ABSTRACT

In an apparatus for continuous draw-off of yarn from a package at a measured rate and under regulated tension, the yarn can either be passed to a waste receptacle for a predetermined length of time or can be metered to a scale for subsequent determination of yarn weight per unit length (denier). Diversion of the running yarn from one path to the other is achieved without affecting yarn draw-off rates and tensions.

4 Claims, 10 Drawing Figures

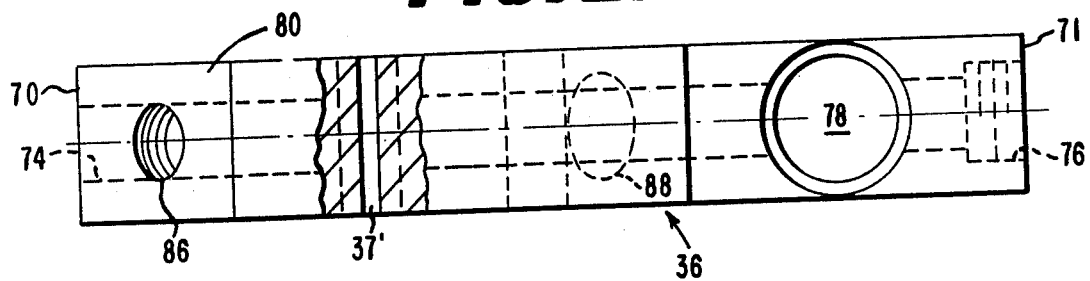
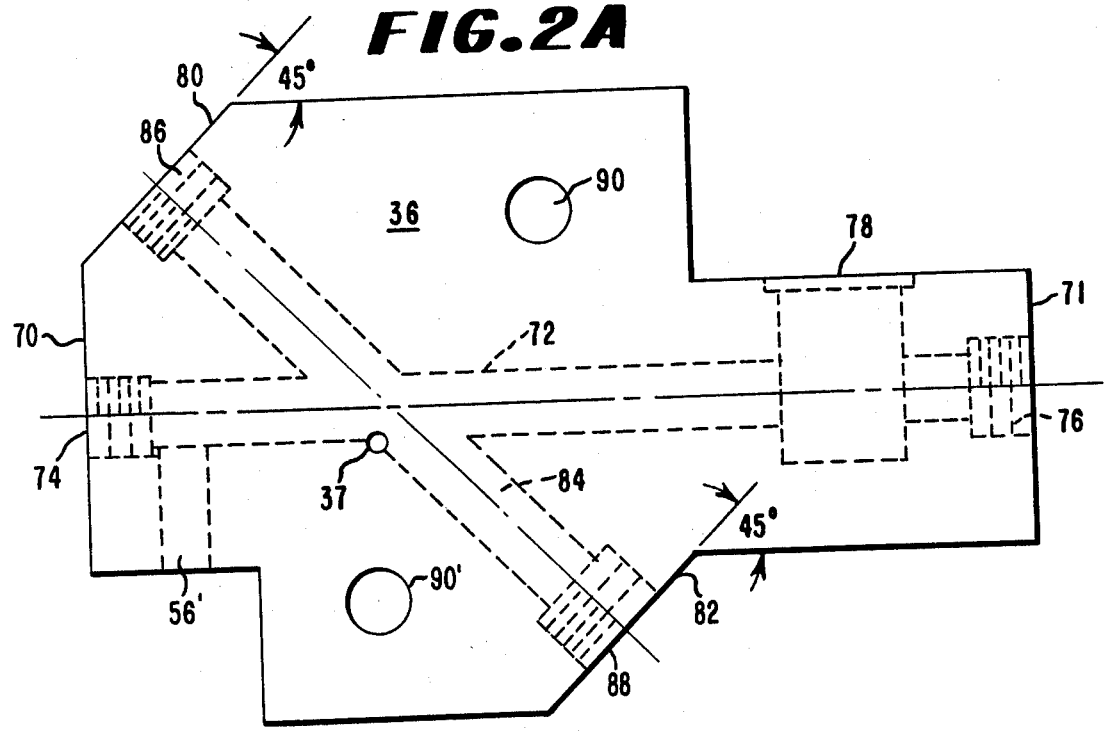
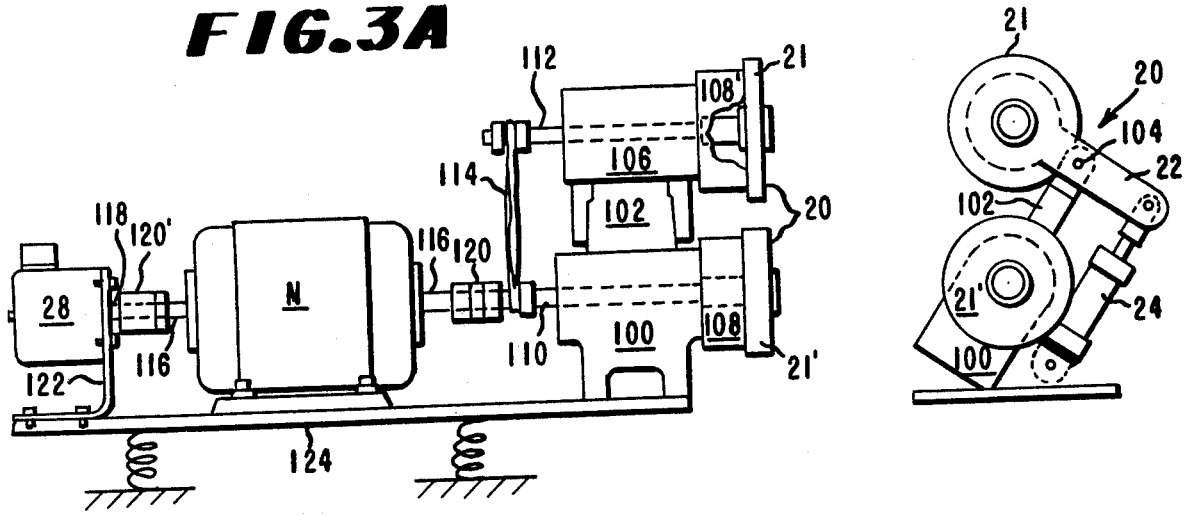

MODES 1 AND 3

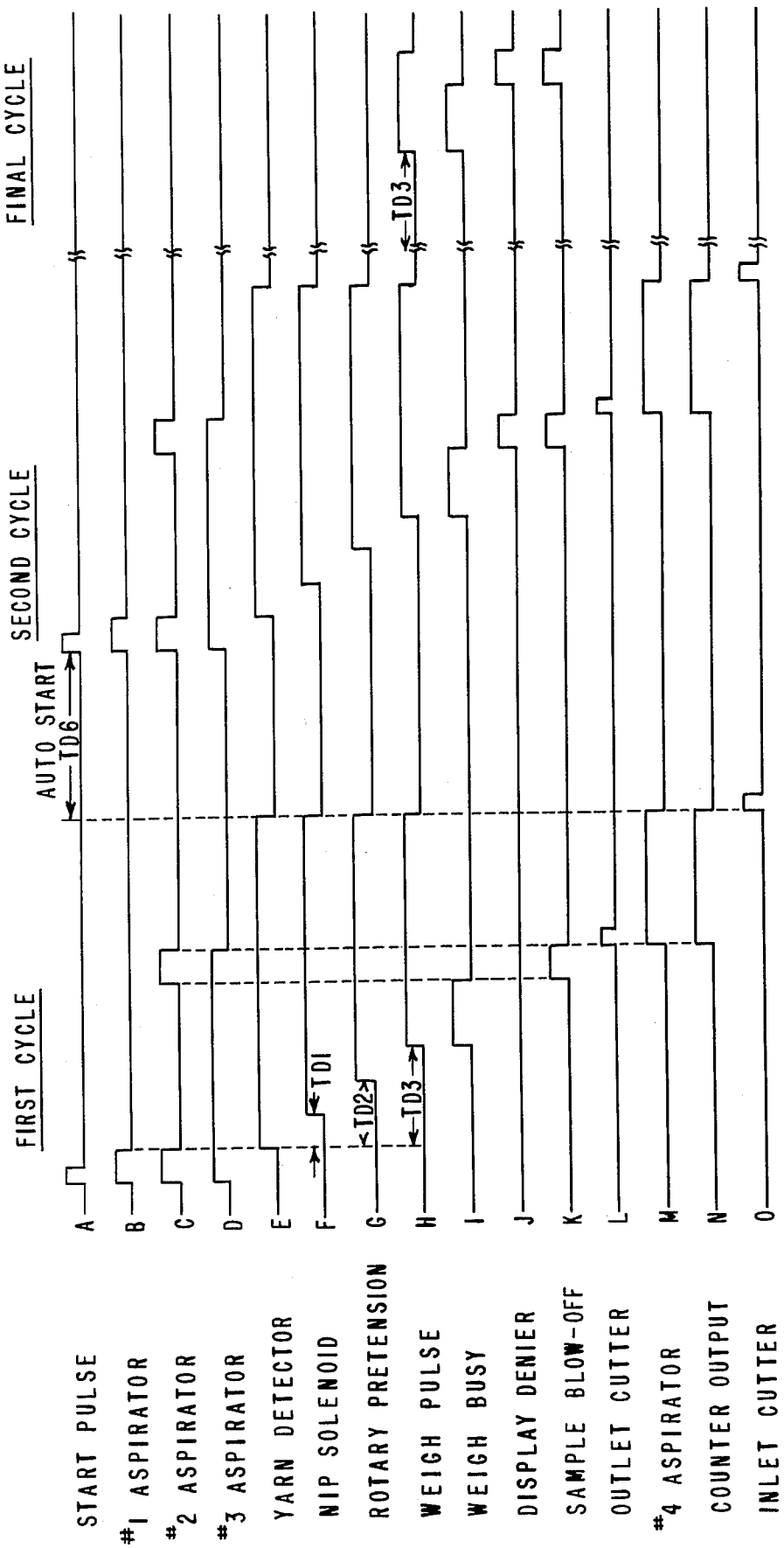

APPARATUS FOR DETERMINING DENIER OF YARN

BACKGROUND OF THE INVENTION

This invention relates generally to apparatus for measuring weight per unit length (e.g., denier) of yarn, and more particularly to an improved, automatic apparatus for prestripping a specified length of yarn from a package, metering a measured length of yarn under constant tension into a scale pan, weighing this specimen to determine the denier therefrom, and finally removing the weighed yarn sample.

In the past, when absolute denier values were required, measurements were usually made by winding a specimen skein of yarn on a reel, manually transferring this specimen to a weighing device, and then computing denier from specimen weight and length. More recently, yarn specimens are prepared by automatically drawing yarn from a package by means of a pair of metering rolls and projecting a measured length of this yarn either into a coiling device or directly onto a pan of a weighing device. One of the problems encountered in deniering yarn is the inaccuracy of measurements experienced when the outside layer of the yarn on the yarn package is used for such measurements. This problem occurs because the yarn on the outside of a yarn package may not only be more likely damaged, but it also may show the effects of tension variations during doffing. Since these in turn affect determination of denier, it is desirable to strip this outer layer from the package and use yarn from a nonexposed portion of the package to assure more accurate denier measurements. To accomplish this requires that yarn be prestripped from the package by some means. Furthermore, when multiple measurements are being made from one package, prior art devices require that the yarn draw-off be stopped when each yarn specimen is cut off, and that the standing part of the yarn which comes from the yarn package source be restrained while the cut yarn specimen is transferred to the weighing pan and/or weighed, even so, yarn length measurement errors arise out of pretension variations resulting from stopping and starting yarn draw-off in the course of a measurement series. This effect is particularly noticeable when measuring high bulk or textured yarns such as BCF, or other easily stretched yarns. Prior art prestripping and measurement techniques are time consuming as well.

The present invention provides a device for continuous draw-off of yarn from a package at a measured rate and under regulated tension. This yarn either is passed to waste for a predetermined length of time or is metered to the pan of a weighing device for subsequent determination of yarn weight per unit length. Diversion of the running yarn from one path to the other is achieved without affecting yarn draw-off rates and tensions.

SUMMARY OF THE INVENTION

In an apparatus for determining denier of yarn that includes a source of supply of said yarn, a scale for weighing a measured length of said yarn, and a transport system for measuring and transferring said measured length of yarn from said source of supply to said scale, a yarn diverter to permit prestripping of said source of supply to a waste receptacle and transferring said measured length of yarn to said scale in a continuous operation said diverter comprising: a block positioned between said transport system, said waste receptacle and said scale, said block having a through passage aligned with said transport system and said waste receptacle and a branch passage leading from an intermediate location on said through passage toward said scale, said through passage having inlet and outlet ends; means for cutting said yarn between said intermediate location and said outlet end; and means for aspirating said through passage both at its inlet and outlet end and said branch passage at its outlet end, according to a preselected operating mode that provides for directing said yarn to said waste receptacle and then to said scale without stopping movement of said yarn.

This apparatus generally includes, in sequence, a first yarn aspirator type sucker gun (designated No. 1 aspirator); a first electrically actuatable cutter; a tensioning device, also electrically actuatable; a pair of metering rolls, one of which is retractable; No. 2 aspirator; a photoelectric yarn sensor; a yarn diverter block arranged either (a) to pass yarn through a second cutter, through No. 3 aspirator to a waste receptacle or (b) sequentially after the second cutter cuts the yarn without stopping the yarn movement, to divert the yarn through No. 4 aspirator to the pan of an automatic weighing device. Whenever the running yarn is diverted to the weighing device, a signalling device on the shaft of one metering roll provides signals to a counter and controller in order to meter a known length of the yarn to the pan. After the first electrically actuatable cutter cuts the yarn upon completion of sample collection, and weighing of the sample is complete, a solenoid operated air nozzle, aimed at the sample on the pan, on command blows the sample toward No. 5 aspirator which exits it to waste. The controller includes logic elements necessary to program solenoids actuating the several aspirators, the two cutters and the tensioning device according to a preselected program. A photoelectric wrap detector monitors the surface of the movable metering roll. Its output is connected to the controller to shut off No. 1 aspirator, actuate No. 1 cutter, and open the tensioning device, in order to arrest yarn being drawn off in case of a roll wrap. A conventional readout component is attached to the weighing device and arranged to record values of denier. Three selectable control programs are provided for sequencing the operation. The first program interrupts yarn draw-off while weighing is being carried out and then resumes yarn draw-off through No. 3 aspirator to waste when weighing of the previous sample is completed. The second program stops and then, after a short delay, automatically restarts the yarn draw-off to waste at the instant each yarn specimen has been collected on the weighing device pan. Stripping to waste continues during the time required for weighing the specimen in order to achieve pretension stabilization before the next specimen is cut and weighed. The third mode is similar to the first, except the metering rolls and pretension device are not used during draw-off to waste. In any case, the transfer from passing yarn to waste and diverting it to the weighing pan is accomplished without interruption in yarn draw-off. Therefore, errors due to interrupting yarn flow and consequent tension fluctuations are eliminated.

BRIEF DESCRIPTION OF THE DRAWINGS

FIGS. 2a and 2b are front elevational and top views, respectively, of a typical diverter block;

FIGS. 3a and 3b are side and front elevational views of the metering rolls assembly;

FIGS. 7a and 7b are timing diagrams for the three operating modes.

DETAILED DESCRIPTION OF THE PREFERRED EMBODIMENT

Figure 1:
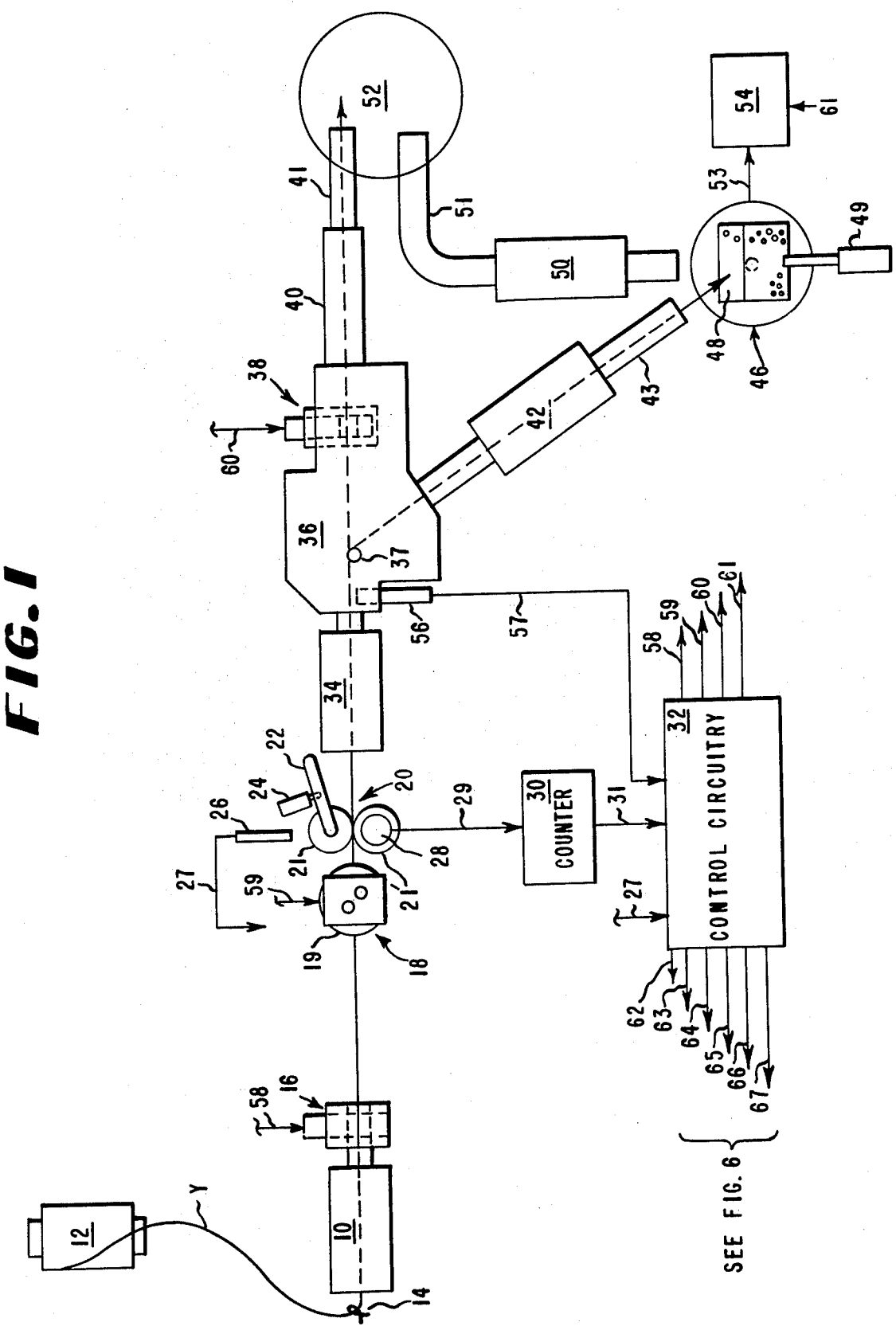
FIG. 1 is a schematic arrangement of the total system.

Details of the preferred embodiment of this invention are shown schematically in FIG. 1 in connection with the overall system for determining yarn weight per unit length. Thus, a first aspirator 10 (e.g., Air-Vac Engg. Co., Model TDH260 yarn handling jet) is mounted, with its axis horizontal, to a framework, not shown, near a guide 14 positioned to receive a yarn "y" from a yarn package 12. A solenoid actuated yarn cutter 16 (e.g., "Plunger Scissors" by Textile Electronics Division, Serviced Electronics, Inc., Greensboro, NC) is connected to the outlet of aspirator 10 to receive yarn therefrom. The yarn passes horizontally next to a releasable tensioning device 18. This device is operated by rotary solenoid 19 (e.g., Cliftonics, Inc., Clifton Springs, N.Y., Model R34-S-261). Next along the horizontal yarn line there is located a metering roll assembly 20 which includes a pair of metering rolls 21, 21'. A lowering arm 22 actuated by air cylinder 24 (e.g., Tom Thumb ®, FAP-3/4-IP, PHD Inc., Fort Wayne, IN) is arranged to lower roll 21 when required. A photoelectric yarn wrap detector 26 (e.g., Scan-A-Matic Corp., Skaneateles, New York, Model S353) is located adjacent roll 21 with its electrical output cable 27 extending to control circuitry 32. A shaft encoder 28 is coupled to the shaft of roll 21'. Encoder 28 may be, for example, Model 711, Encoder Products, Co., Sand Point, ID. The electrical output from encoder 28 is carried over electric cable 29 to counter 30 and thence over line 31 to control circuitry 32. A second aspirator 34 is located along the horizontal yarn line extending from metering roll assembly 20. Aspirator 34 is connected to diverter block 36 which has a horizontal channel extending therethrough and near photo-electric yarn detector 56 (typically a Skan-A-Matic Model S353), its output extending over line 57 to control 32. Joining the through channel is a branch channel at 45° descending downwardly. A ceramic pin 37 extends through the diverter block and is used to reduce wear at the junction line of the two channels. A second solenoid actuated yarn cutter 38 is located along the horizontal passage of diverter block 36 near its exit end. A third aspirator 40 (Model TDH260 or, for heavy yarn, TDRH-380 Air-Vac Engg. Co.) is located along the horizontal yarn line and has an exit pipe 41 extending to a waste receptacle 52. A similar, fourth, aspirator 42 is located at the outlet of the 45° passage from diverter block 36 and has an exit pipe 43 extending to a point adjacent the opening 128 (FIG. 4) in weighing pan 48 of automatic weighing device 46 (e.g., Scientech, Inc., Boulder, CO, Model 222-007). An air jet 49 and fifth aspirator 50 are aligned on opposite sides of pan 48 so that air jet 49 can blow a yarn sample from pan 48 to aspirator 50. These are actuated by a single solenoid air valve. Aspirator 50 is, for example, Air-Vac Engg. Co., Model TDRH-1000. The exit pipe 51 from aspirator 50 extends to waste receptacle 52. Output signals from weighing device 46 extend over cable 53 to read-out device 54 (e.g., the read-out component of a Scientech, Inc., balance system).

Figure 7A:
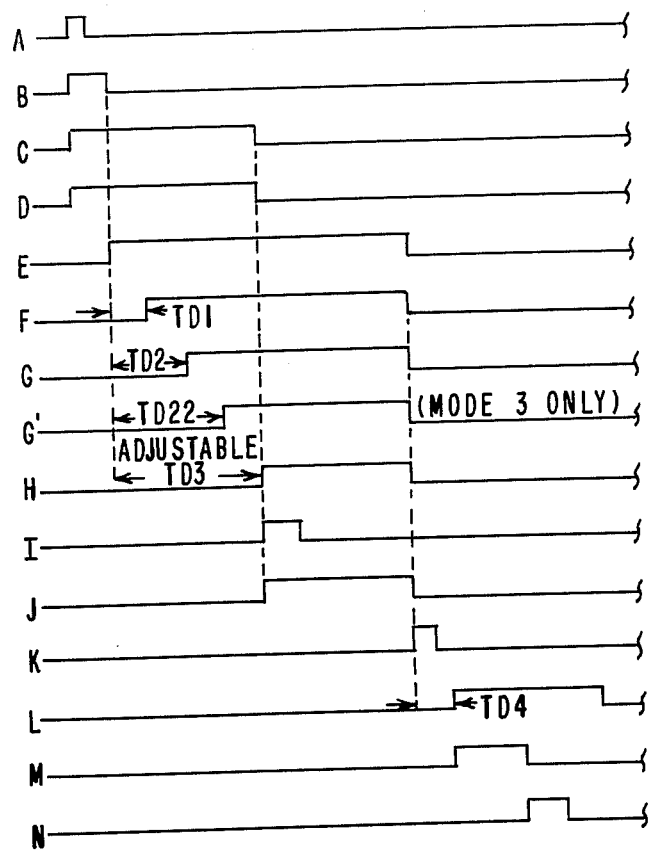

Finally, control circuit 32 containing logic circuitry (e.g., DEC K logic or a microcomputer) is arranged to produce the control signals shown in the timing diagrams of FIGS. 7a and 7b. In operation, using the input signals from the two photoelectric yarn detectors 26, 56, and counter 30 appearing on lines 27, 57 and 31, respectively, the control logic generates output signals needed to coordinate and control the operation of the several aspirators, the two cutters, the tensioning device, the metering roll assembly, the weighing device and the sample removal airjet. These signals appear on lines 58 through 67 connecting control circuit 32 to the elements recited. More specifically, control signals on lines 62 through 67 are used to operate the various solenoid actuated valves shown in FIG. 6, whereas control signals on lines 58 through 61 operate cutter 16, tensioner 18, cutter 38 and weighing device 46, respectively.

Turning now to FIGS. 2a, 2b, the structure of diverter block 36 is seen to include first and second vertical faces 70, 71 providing the entrance and first exit faces of the block. A horizontal passage 72 is bored through the block extending from face 70 to face 71. The inlet end of this passage is threaded at 74 to receive mating portion of aspirator 34. Similarly, a threaded portion 76 is provided at the outlet end of passage 72 to receive mating portion of the entrance end of aspirator 40. A vertical bore 78 is provided near the exit end of block 36 and shaped to receive yarn cutting device 38. The upper corner of the entrance end of block 36 is cut off at a 45° angle to provide first sloping face 80. A second 45° sloping face 82 is provided adjacent the lower face of the block and in opposition to face 80 so that a second passage 84 is bored through block 36 so as to intersect passage 72 at a 45° angle intermediate its ends. A first threaded portion 88 is provided in the exit end of passage 84 and constructed to receive mating portion of the entrance end of aspirator 42. A second threaded portion 86 is provided in the opposite end of passage 84 to receive a threaded plug used to permit access to passage 84 for cleaning. Mounting holes 90, 90' are provided for use in fastening block 36 to the frame (not shown) of the system. A bore 37' (FIG. 2b) is provided through the thickness of block 36 to receive ceramic guide 37. Hole 37' is located at the intersection of passages 72 and 84 at the point where yarn when entering through passage 72 at face 70 and exiting through passage 84 at face 82 would normally contact the passage juncture. Another bore 56' extends from the bottom face of block 36 up to reach passage 72 and is shaped to receive detector 56.

Details of the metering rolls assembly 20 are provided by FIGS. 3a, 3b. The lower roll 21' is mounted on a shaft in bearings held in fixed bracket 100. Extension 102 projects upward and backward from bracket 100 and is arranged to pivotably mount arm 22 about pin 104. One end of arm 22 is arranged to hold movable bearing bracket 106. The other end of arm 22 carries the plunger portion of air cylinder 24. Brackets 100, 106 carry nonrotating yarn shields 108, 108'. Drive shafts 110, 112 extend backward from brackets 100, 106 to provide for driving the rolls 21', 21, respectively. A drive belt 114 of elastomeric material is stretched between shafts 110 and 112. An electric motor M with shaft 116 is coupled at one end to shaft 110 and at the other end to shaft 118 of shaft encoder 28 by means of conventional couplers 120, 120'. Encoder 28 is mounted on bracket 122 which, along with the base of motor M and roll bracket 100, is fixed to a system base 124.

Figure 4:
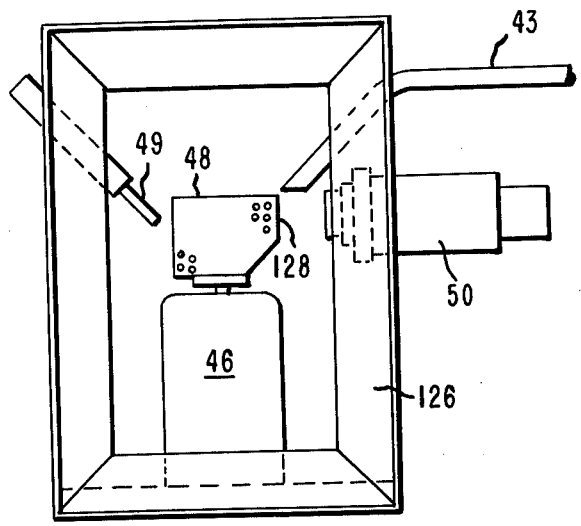
FIG. 4 is a front elevational view of the weighing and sample collection system.

The scale portion of the weighing system is seen from FIG. 4 to include an enclosure 126 in which the automatic weighing device 46 is placed. A sample receiving weighing pan 48 rests on weighing device 46. This pan has an open section 128 located at one side and is formed of perforated or screen material in order to trap yarn but allow air to pass therethrough. The exit end of pipe 43 extending from aspirator 42 is located adjacent the open side 128 of pan 48. In a similar manner, the entrance end of aspirator 50 is located near hole 128. On the other side of pan 48 and at an angle with the entrance of aspirator 50 there is located the air nozzle 49 which is arranged to blow against the solid bottom of pan 48 to push the yarn sample up the slope from the pan bottom toward the entrance end of jet 50.

Figure 5:
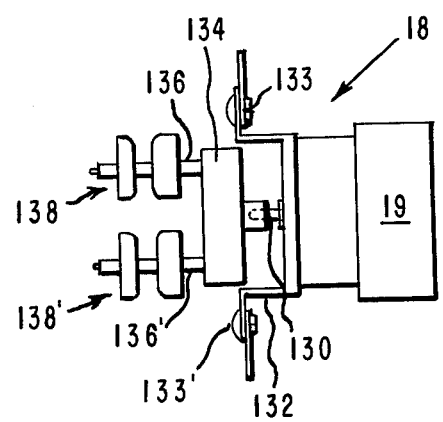
FIG. 5 is a side elevational view of the tensioning device for the heavy denier yarns.

The structure of the releasable tensioning device is shown in FIG. 5 to include a rotary solenoid 19 having an output shaft 130 extending through a mounting bracket 132 fixed to the system frame by means of fasteners 133, 133'. A tension arm holder 134 is fastened to output shaft 130 by conventional arrangements and is provided with two tension arms 136, 136' which in turn carry tensioning devices 138, 138'. Devices 138, 138' take the form of tensioning disks with electromagnetic adjustment means (e.g., Lindly, Model 414) which are used when the instrument is operated to measure heavy denier yarns, bulk yarns or textured yarns. However, when the instrument is arranged for measurements of light denier hard yarns, the disk tensioners are replaced by ceramic yarn guide pins, extending out from arms 136, 136'. Thus, the tensioning device operates when the rotary solenoid is actuated to rotate tension arm holder 134 so as to require the yarn originally passing between the two tension devices 138, 138' to form an S-shaped path and thereby increase the tension in the yarn beyond the tensioning device to a preselected level.

Figure 6:
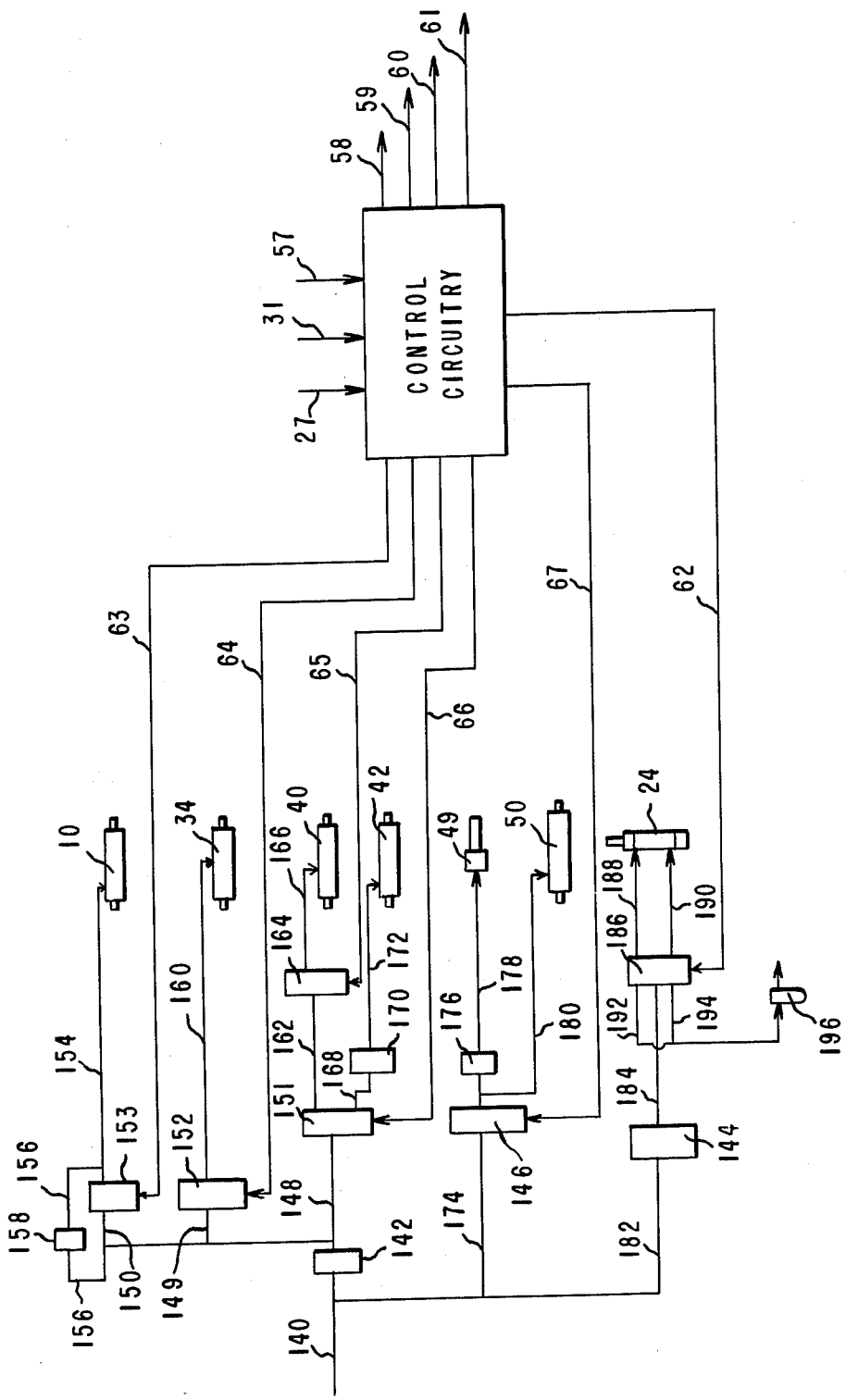
FIG. 6 is a pneumatic control diagram.

FIG. 6 provides details of the pneumatic and electrical system for the programmed automatic control of the overall measuring system. Thus, compressed air is received from a source not shown over air conduit 140 which branches to go to first filter regulator 142 and at the same time over conduit 182 to a second identical, filter regulator 144 (e.g., Model BO4-202-MIK-AU manufactured by C. A. Norgren Co.). A third branch goes over conduit 174 to a two-way solenoid valve 146 (e.g., Model 20503-302U manufactured by Schrader/Scovill Mfg. Co., Wake Forest, NC). Output from regulator 142 extends over conduits 148, 149, and 150 to the air input sides of solenoid actuated valves 151, 152 and 153, respectively. Valve 151 is a four-way valve (e.g., Model 52001-112, Schrader/Scovill Mfg. Co.) and valves 152 and 153 are two-way valves (e.g., Model 20503-3024, of the Schrader/Scovill Mfg. Co.). One output from valve 153 extends over conduit 154 to the air input connection of No. 1 aspirator 10. A bleed conduit 156 containing a variable air restricter 158 (e.g., Model 3312H4B of Hoke Inc., Creskill, NJ), is connected between the input and output conduits of valve 153. The output of valve 152 is conducted over conduit 160 to the input fitting of No. 2 aspirator 34.

A first output from solenoid actuated valve 151 extends over air conduit 162 to the input side of waste solenoid valve 164 (e.g., two-way valve Model 20503-3024 manufactured by Schrader/Scovill Mfg. Co.). The output from this outer valve is conducted over air conduit 166 to the previously mentioned waste aspirator 40. The second output from valve 151 extends over conduit 168 through filter regulator 170 (same as regulators 142, 144) and thence over air conduit 172 to the air input connection of diverter aspirator 42. A branch air conduit 174 extends from the air supply line 140 to the input side of two-way solenoid valve 146 (e.g., Model 20503-3024 of Schrader/Scovill Mfg. Co.), the output of which extends first through regulator 176 (e.g., Model BO4-202-MiK-AU of C. A. Norgren Co., Inc.) and over air conduit 178 to the air input side of sample removal jet nozzle 49. The output from valve 146 also extends over air conduit 180 to the air input connection of sample removal aspirator 50.

Another branch air conduit 182 extends from air supply 140 to filter regulator 144, the output line of which extends over air conduit 184 to the input side of solenoid valve 186. This is a four-way solenoid actuated air valve (e.g., Model 52001-112 of the Schrader/Scovill Mfg. Co.). Air supply outputs from valve 186 are selectively supplied over air conduits 188 or 190 to respective input connections for air cylinder 24. Exhaust outlets from valve 186 are connected over air conduits 192, 194 to oil removal filter 196 (e.g., Model F44-200-MOTA of C. A. Norgren Co.).

In operation, a selector switch not shown in control circuit 32, is provided to enable the operator to select one of three operating modes afforded by this circuitry. In the first and third modes (FIG. 7a), a sample length from a yarn package is drawn-off to waste, then the sample is cut and, without stopping the motion of the yarn, the end is diverted through a No. 4 aspirator 42 whereupon it is metered and collected on the weighing pan. After the specimen is cut to a predetermined length it is weighed and read out while at the same time the yarn end is held in a No. 1 aspirator 10 to facilitate string-up should another specimen be needed from the same package. The second mode (FIG. 7b) provides for running multiple samples from the same package of from different packages where significant prestripping is necessary between samples. In this mode, measurement time is conserved by providing an overlap in the time that a new sample is being run to waste while the previous sample is being weighed.

Referring to FIGS. 1 and 7a, the first and third operating modes provide for automatically threading the yarn end of a package to be sampled through the system, stripping off a portion of it, then cutting and weighing it in the following manner.

The operator closes a start switch, producing a start pulse, waveform A, which simultaneously (1) turns on the air to No. 1 aspirator 10, waveform B, which in turn feeds the end of yarn extending from package 12 and projects it through open cutter 16, through pretensioning device 18 and between the normally open and rotating metering rolls 21 and 21'; (2) turns on the air to No. 2 aspirator 34, waveform C, which in turn projects the yarn, appearing at its inlet, through diverter block 36 and open cutter 38; and (3) turns on the air to No. 3 aspirator 40, waveform D, which draws the yarn from cutter 38 and projects it to waste receptacle 52 through pipe 41. At the instant photodetector 56 senses the yarn end, waveform E, the following sequence of events is triggered: (1) air to No. 1 aspirator 10 is turned off, waveform B, (2) the piston from air cylinder 24 is extended to close the nip of metering rolls 21, 21' after a delay of TD1 seconds, waveform F, (3) the tension arm holder 134 (FIG. 5) of tensioning device 18 is rotated a predetermined amount after a delay of TD2 seconds to cause the running yarn to pass around portions of tension arms 136, 136' thereby maintaining constant tension in the yarn up to the nip rolls, waveform G (in addition, for mode 3 operation, tension disks 138, 138' close after an additional delay of TD22 seconds, shown in waveform G') and (4) air to No. 4 aspirator 42 is turned on after an adjustable delay of TD3 seconds to divert the running yarn to the weighing pan 48. At the instant aspirator 42 turns on, four events occur simultaneously, namely (1) the air to No. 2 aspirator 34 is turned off, waveform C, (2) the air to No. 3 aspirator 40 is turned off, waveform D, (3) outlet cutter 38 cuts the yarn, waveform I, and (4) counter 30 is started counting the length increment pulses from shaft encoder 28, waveform J. At the end of a preselected count on counter 30, waveform J, the following events occur simultaneously: (1) inlet cutter 16 is operated, waveform K, (2) metering roll 21 is raised by cylinder 24, waveform F, (3) pretension of both arms and disks is released, waveforms G and G', respectively, and (4) the air to No. 4 aspirator 42 is turned off, waveform H. After a delay of TD4 seconds, the automatic weighing device 46 is activated by a weigh pulse, waveform L. During the settling period, a weigh busy signal, waveform M, is used to disable the readout for a predetermined period before displaying the denier reading and blowing off the yarn specimen to waste by the combined action of jet 49 and aspirator 50. This occurs during the time interval shown in waveform N.

In order to facilitate string-up, if additional measurements are to be made from the just sampled package, a small amount of bleed air from air conduit 156 (FIG. 6) may be used to provide a small holding force to maintain the yarn end in No. 1 aspirator 10 after the main air is disconnected as noted above. Bleed air is also useful when exchanging yarn packages. After cutting off the old yarn end near package 12, the bleed air at No. 1 aspirator 10 is sufficient to hold the cut segment in place. When the start button is pushed for the next sample, the cut segment is blown through the system to waste. When the new end from the next yarn package is brought near the inlet of No. 1 aspirator 10, it is immediately sucked into it and the next measurement cycle starts.

Referring to FIG. 7b and FIG. 1, mode 2 operations are initiated when the operator closes the start switch thus producing a start pulse, waveform A. This pulse simultaneously (1) turns on the air to No. 1 aspirator 10, waveform B, (2) turns on the air to No. 2 aspirator 34, waveform C, and (3) turns on the air to No. 3 aspirator 40, waveform D. Air to these aspirators causes the yarn end to move from the package 12 through the system to waste receptacle 52 in a similar fashion to mode 1 and 3 operations described previously. At the instant photodetector 56 senses the yarn end, waveform E, the following sequence of events is triggered: (1) air to No. 1 aspirator 10 is turned off, waveform B, (2) air to No. 2 aspirator 34 is turned off, waveform C, (3) the nip of metering rolls 21 and 21' is closed after a delay of TD1 seconds, waveform F, (4) the tension arm holder 134 (FIG. 5) in tensioning device 18 is rotated a predetermined amount after a delay of TD2 seconds, waveform G, and (5) after a further delay of TD3 seconds, the automatic weighing device 46 is activated by weigh pulse, waveform H. At this point in the first cycle it is apparent that since no yarn has been diverted to the weighing pan for measurement, weighing empty weighing pan 48 would be meaningless. To compensate for this condition, no display denier signal, waveform J, is used at the end of the first cycle weigh busy signal, waveform I. The trailing edge of the weigh busy signal, waveform I, is used, however, to turn on the air to No. 2 aspirator 34 and the combination sample blow-off jet 49 and aspirator 50 to ensure weighing pan 48 is clear before it receives the first sample. The occurrence of the trailing edge of the sample blow-off pulse, waveform K, initiates the following simultaneous events: (1) the air to No. 2 aspirator 34 is turned off, waveform C, (2) the air to No. 3 aspirator 40 is turned off, waveform D, (3) outlet cutter 38 is operated to sever the running yarn to waste, waveform L, (4) the air to No. 4 aspirator 42 is turned on to divert the running yarn to weighing device 46, waveform M, and (5) counter 30 is started counting the length increment pulses from shaft encoder 28, waveform N. At the end of a preselected count on counter 30, waveform N, the following events occur simultaneously: (1) inlet cutter 16 cuts the running yarn, waveform O, (2) the nip between metering rolls 21 and 21' opens, waveform F, (3) the pretension is released, waveform G, (4) weigh pulse, waveform H, turns off, (5) the air to No. 4 aspirator 42 is turned off, waveform M and (6) a time delay of TD6 seconds is initiated to start the next strip-cut-weigh cycle, waveform A.

The second and succeeding cycles are repeats of the first with the exception of the display denier signal, waveform J, as mentioned earlier, whereas the final cycle uses just the control signals needed to carry out the weighing operation on the specimen deposited on weighing pan 48 at the end of the previous cycle, waveform H, I, J and K.

In all modes of operation, not only is the yarn projected to waste under a prescribed tension, but it is also cut and diverted to the weighing pan under essentially the same tension condition. Since yarn tension fluctuations during the metering of a specimen to be weighed, if permitted, would proportionally change the weight per unit length determination (due to variations in metered length), this device provides a novel means to overcome this measurement limitation during the entire time that a test specimen is being gathered. This has the important consequence of providing a significant increase in the precision of measurement of yarn weight per unit length when a cut and weigh technique is used, particularly for high bulk or textured yarns such as BCF, or other easily stretched yarn structures.

What is claimed is:

1. In an apparatus for determining denier of yarn that includes a source of supply of said yarn, a scale for weighing a measured length of said yarn, and a transport system for measuring and transferring said measured length of yarn from said source of supply to said scale, a yarn diverter to permit stripping of said source of supply to a waste receptacle and transferring said measured length of yarn to said scale in a continuous operation, said yarn diverter comprising: a block positioned between said transport system, said waste receptacle and said scale, said block having a through passage aligned with said transport system and said waste receptacle and a branch passage leading from an intermediate location on said through passage toward said scale, said through passage having inlet and outlet ends; means for cutting said yarn between said intermediate location and said outlet end; and means for aspirating said through passage both at its inlet and outlet end and said branch passage at its outlet end according to a preselected operating mode that provides for directing said yarn to said waste receptacle and then to said scale without stopping movement of said yarn.

2. The apparatus as defined in claim 1, including a yarn detector located between said intermediate location on said through passage and said inlet end thereof.

3. The apparatus as defined in claim 1 including a tensioning device located between said source of supply and said transport system, said tensioning device applying a preselected tension to said yarn during transport of said measured length.

4. The apparatus as defined in claim 3 including a yarn cutter located between the source of supply and said tensioning device.

* * * * *